(12) United States Patent  (10) Patent No.: US 7,607,917 B2
Virnicchi et al.  (45) Date of Patent: Oct. 27, 2009

(54) CHEEK AND LIP RETRACTOR

(75) Inventors: Tommaso Virnicchi, Recanati (IT); Eros Nanni, Castel Guelfo di Bologna (IT)

(73) Assignee: Cefla Societa' Cooperativa, Imola (IT)

( * ) Notice: Subject to any disclaimer, the term of this patent is extended or adjusted under 35 U.S.C. 154(b) by 34 days.

(21) Appl. No.: 11/572,184

(22) PCT Filed: Jul. 15, 2005

(86) PCT No.: PCT/EP2005/053422

§ 371 (c)(1),
(2), (4) Date: Jul. 25, 2007

(87) PCT Pub. No.: WO2006/008278

PCT Pub. Date: Jan. 26, 2006

(65) Prior Publication Data

US 2008/0096165 A1  Apr. 24, 2008

(30) Foreign Application Priority Data

Jul. 16, 2004 (IT) .......................... BO2004A0443

(51) Int. Cl.
*A61C 1/00* (2006.01)
*A61C 3/00* (2006.01)
(52) U.S. Cl. .................. 433/29; 433/140; 600/201; 600/208; 600/212; 600/223; 600/237; 600/242
(58) Field of Classification Search ............ 433/29, 433/140; 600/201, 208, 212, 223, 237, 242, 600/249
See application file for complete search history.

(56) References Cited

U.S. PATENT DOCUMENTS

| 4,592,344 | A | | 6/1986 | Scheer |
| 4,889,490 | A | * | 12/1989 | Jenkinson .................. 433/136 |
| 6,228,025 | B1 | | 5/2001 | Hipps et al. |
| 2003/0143512 | A1 | * | 7/2003 | Hirsch et al. ................. 433/93 |

FOREIGN PATENT DOCUMENTS

| WO | WO 02/07632 A | 1/2002 |
| WO | WO 03/082123 A | 10/2003 |
| WO | WO 03082123 A2 * | 10/2003 |

OTHER PUBLICATIONS

Machine translation of WO 03/082123 A2.*

* cited by examiner

*Primary Examiner*—Chris L Rodriguez
*Assistant Examiner*—Matthew M Nelson
(74) *Attorney, Agent, or Firm*—Hogan & Hartson LLP

(57) ABSTRACT

A cheek and lip retractor is defined by a supporting member supporting a pair of retracting elements to be inserted at least partially in a patient's mouth, with a light source housed in the supporting member. An optical device for the transmission of the light emitted from the light source inside the mouth extends along the supporting member and/or along the retracting elements.

8 Claims, 4 Drawing Sheets

CHEEK AND LIP RETRACTOR

TECHNICAL FIELD

The present invention relates to a cheek and lip retractor.

BACKGROUND ART

In dentistry, a cheek and lip retractor is used, comprising: a couple of retracting elements, the couple of retracting elements being apt to be at least partially inserted in the mouth of a patient; a supporting element for the retracting elements; and an illuminating device for the patient's mouth.

Generally, the illuminating device comprises at least a remote light source disposed at a given distance from both the supporting element and the retracting elements, and a fibre optic device for the transmission of the light emitted from the light source to the mouth.

Known cheek and lip retractors of the above described type show some drawbacks mainly due to the fact that said fibre optics are relatively heavy and cumbersome, therefore making the use of said retractors uncomfortable and awkward.

As fibre optics come into contact with patient's mouth and, therefore, must be sterilised, known cheek and lip retractors of the above type present, moreover, the further drawback that sterilisation damages rapidly fibre optics and requires frequent substitutions of the fibre optics themselves.

DISCLOSURE OF INVENTION

It is an object of the present invention to provide a cheek and lip retractor free of the above mentioned drawbacks and of simple and economic construction.

According to present invention, there is provided a cheek and lip retractor as claimed in claim 1.

BRIEF DESCRIPTION OF THE DRAWINGS

A non-limiting embodiment of the present invention will be described by way of example with reference to the accompanying drawings, in which.

BEST MODE FOR CARRYING OUT THE INVENTION

Figure 1:
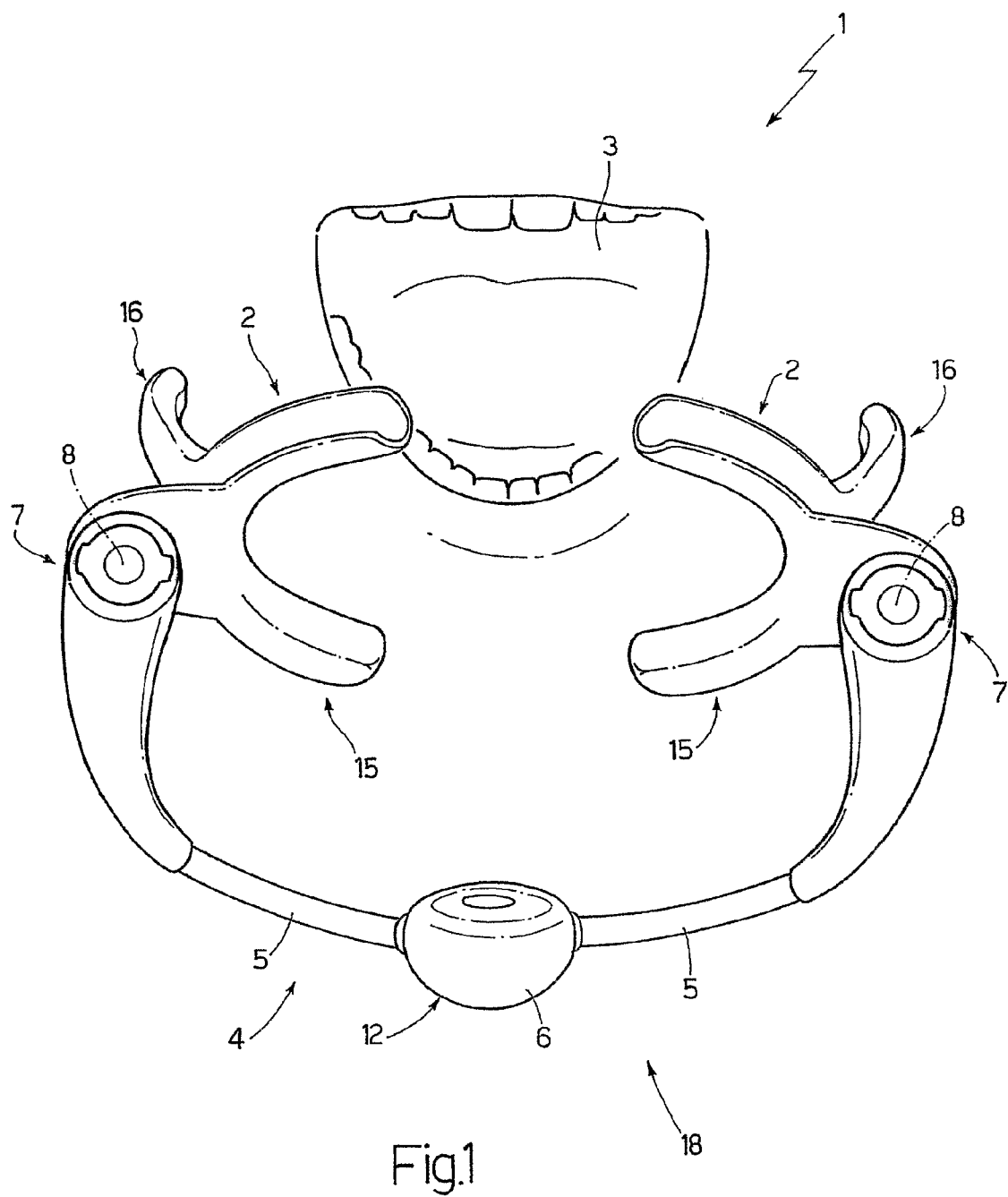
FIG. 1 is a perspective schematic view of a preferred embodiment of cheek and lip retractor of the present invention.

Number 1 in FIG. 1 indicates as a whole a cheek and lip retractor comprising a couple of retracting elements 2 that can be inserted at least partially in a patient's mouth 3 and a supporting member 4 of the retracting elements 2.

Member 4 comprises two supporting elements 5, which extend from opposite sides of a housing 6, are substantially arched in shape, are elastically deformable, and are realised, for instance, with at least a metallic wire (not illustrated), coated with a polymeric material.

Figure 5:
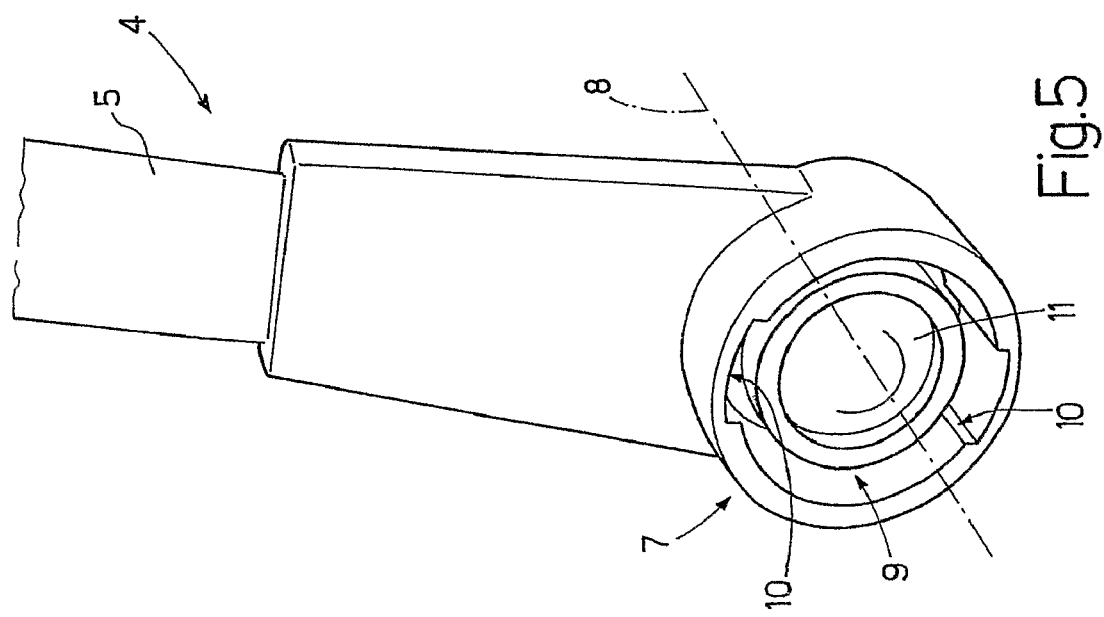
FIG. 5 is a second perspective schematic view of the detail of FIG. 4.

With reference to FIG. 5, each element 5 presents a free end 7, which is substantially cylindrical, has a given longitudinal axis 8, and is internally delimited by a surface 9 coaxial with axis 8. Surface 9 is provided with two cavities 10, which extend parallel to axis 8, and are uniformly distributed around axis 8 itself.

End 7 houses in its interior, in a position substantially coaxial to axis 8, a light source defined by a LED 11 (in the case in point a high efficiency white LED) electrically connected to a supply and control device 12 housed in the housing 6 through an electric conductor defined by said metallic wire (not illustrated) contained in element 5.

Figure 2:
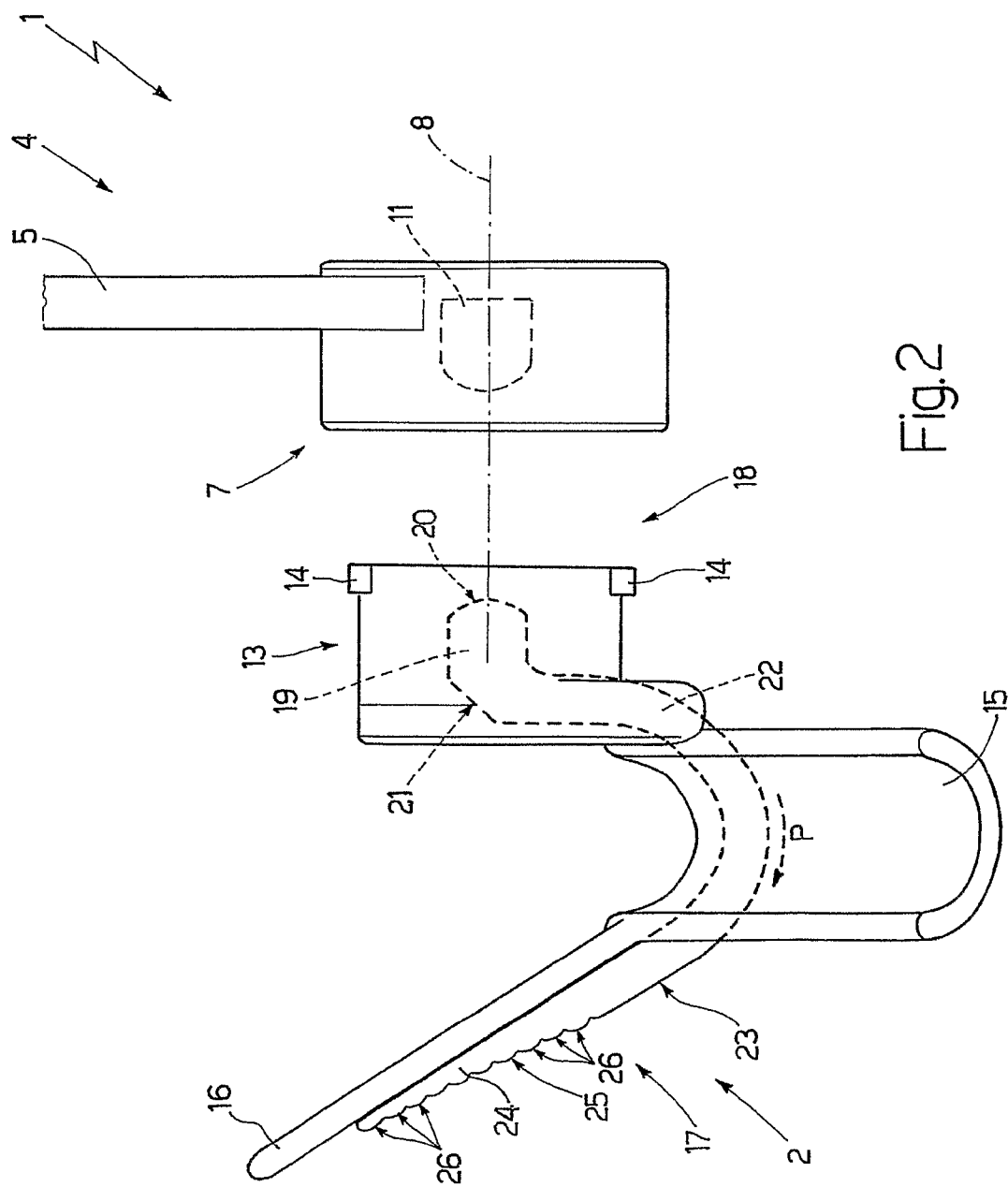
FIG. 2 is an exploded lateral view of the cheek and lip retractor of FIG. 1.

With reference to FIGS. 1 and 2, each element 2 comprises a tubular hub 13, which engages the relative end 7 coaxially with axis 8, extends around relative LED 11, and presents two teeth 14, which radially protrude towards outside from the external surface of hub 13, are uniformly distributed around axis 8, and are apt to engage the relative cavities 10 after an axial displacement introducing hub 13 in the interior of relative end 7. After axial displacement for introducing hub 13 in end 7, teeth 14 release cavities 10, and allow the user to rotate elements 2 relative to elements 5 and to set elements 2 in a determined angular position around axis 8.

Element 2 comprises, moreover, a first elongated portion 15, which is connected at an intermediate point to hub 13, extends in a plane substantially orthogonal to axis 8, presents a substantially semi-toroidal shape and has a transverse section of substantial semi-cylindrical shape so that it can engage, while in use, the patient's lips. Element 2 comprises, finally, a second elongated portion 16, which extends from the opposite side of hub 13 from an intermediate point of portion 15, and is apt to engage, while in use, patient's cheeks.

Each element 2 is made, in the case in point, in a polymeric transparent material, and is shaped so that it defines an optical device 17 for the transmission of the light emitted by relative LED 11 inside mouth 3.

Supply and control device 12, optical devices 17, LEDs 11, and said electrical conductors (not illustrated) inserted in the interior of supporting elements 5 define, therefore, a device 18 for the illumination of mouth 3.

Each device 17 is apt to supply the light emitted from relative LED 11 for total internal reflection, and extends along a defined path P comprising a first tract 19 substantially cylindrical, which is placed internally to relative hub 13 facing relative LED 11, and extends coaxially to relative axis 8.

Tract 19 is apt to transmit the light emitted by relative LED 11 parallely to relative axis 8 and is axially limited, at its first end, by a convex surface 20 placed with its convexity facing relative LED 11, and, at its second end, by a prismatic surface 21 placed so that it can deviate light of substantially 90° with respect to relative axis 8 itself.

Path P comprises, moreover, a second tract 22, which extends in part perpendicularly to axis 8 and in part around portion 15, and is limited externally by a substantially smooth surface 23 apt to ensure light transmission for total internal reflection.

According to a non illustrated embodiment, tract 22 extends both around portion 15 (as illustrated in FIG. 2) and along portion 15 itself.

Path P comprises, finally, a third tract 24, which comes after tract 22, extends along portion 16, and is limited externally by a surface 25 having protrusions 26 distributed along surface 25 itself to deviate light and to light up, therefore, mouth 3.

Figure 3:
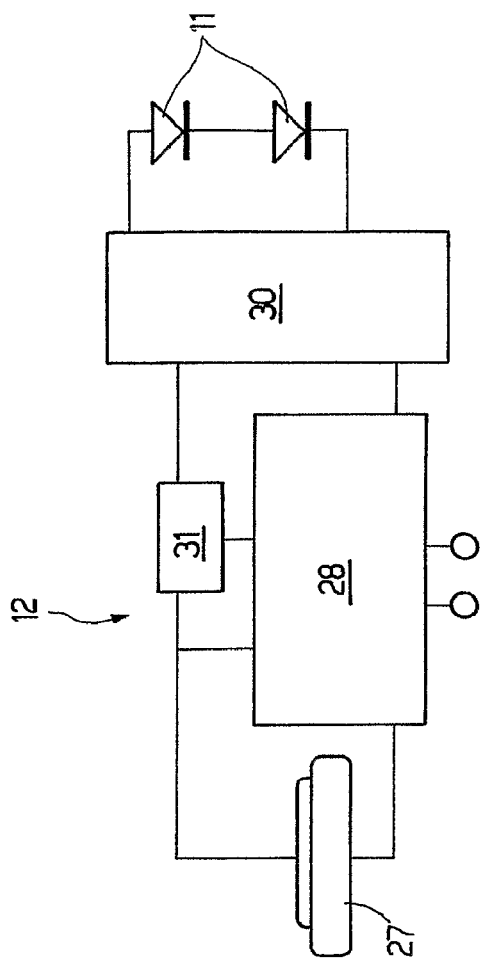
FIG. 3 is a block diagram of an electric circuit inserted in the cheek and lip retractor of FIGS. 1 and 2.
Figure 4:
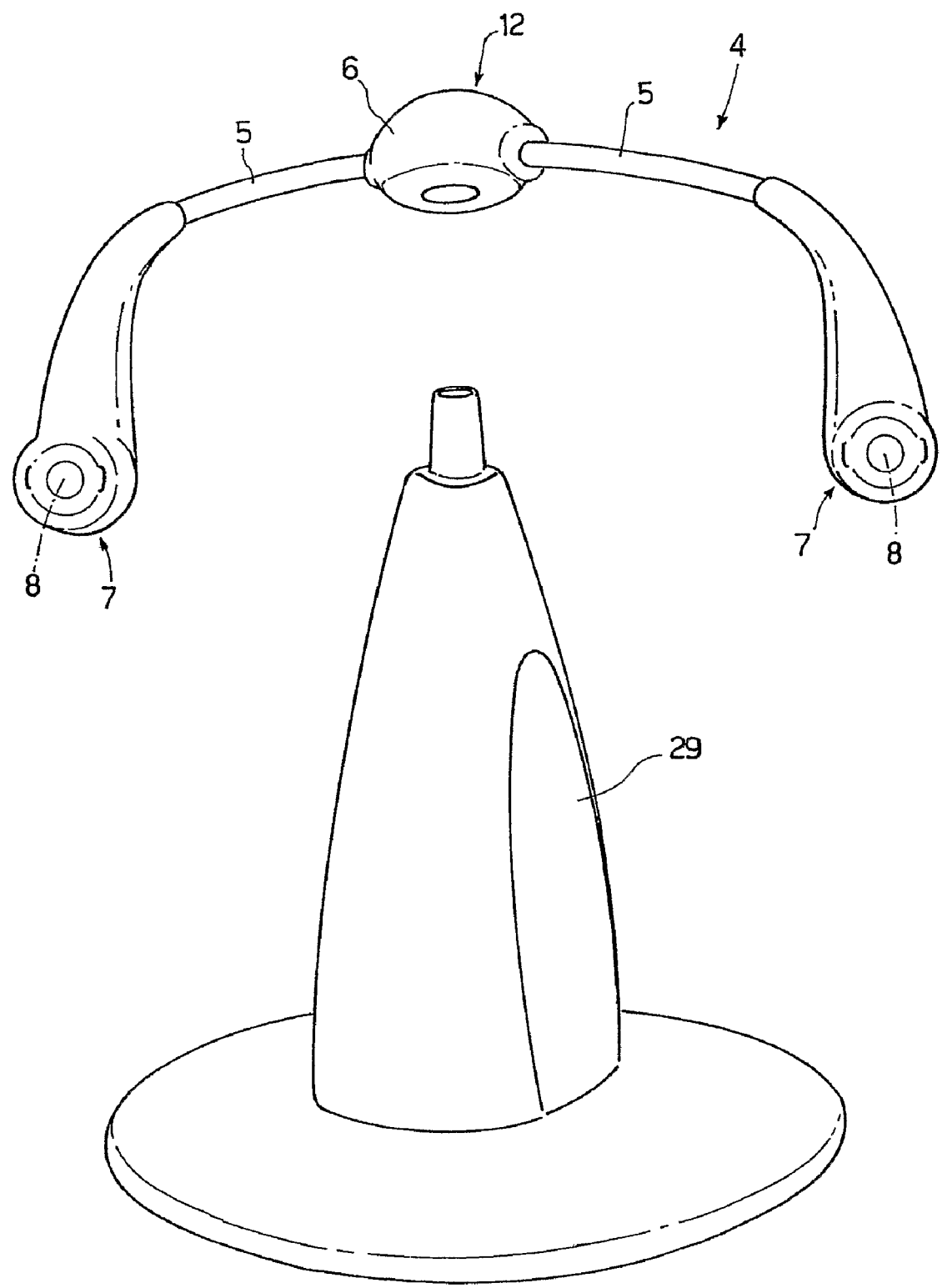
FIG. 4 is a first perspective schematic view of a detail of the retractor of FIGS. 1 and 2 and of a relative recharge device.

With reference to FIG. 3, device 12 comprises a rechargeable battery 27 with:

a first electronic circuit 28 apt to manage the recharge phase of battery 27 when element 4 is laid over a recharge base 29 (FIG. 4), a second electronic circuit 30 apt to manage the discharge phase of battery 27 and to supply LEDs 11 with a constant electric energy, and a third electronic circuit 31 apt to keep LEDs 11 switched off when element 4 is laid on base 29 and device 18 for the illumination of mouth 3 is switched on.

From all said above, it follows that cheek and lip retractor 1 is comparatively compact, easy to handle, and economic. Moreover, since elements 2 are releasably coupled to supporting element 4, it is possible:

to sterilise only the parts of cheek and lip retractor 1 that come into contact with mouth 3, that is the retracting elements 2, thus avoiding to sterilise element 4 and, therefore, to damage the electrical parts mounted on element 4 itself;

to easily substitute the retracting elements 2 with new retracting elements 2 both according to patient's mouth dimensions, and in case of sterilisation of retracting elements 2 themselves; and to substitute, when necessary, damaged retracting elements 2 at a relatively low cost.

The invention claimed is:

1. A cheek and lip retractor comprising:

retracting means for at least partially inserting in a patient's mouth;

supporting means for releasably retaining and supporting said retracting means, said supporting means including a seat portion; and an illuminating device for illuminating the patient's mouth, said illuminating device including a light source fixed to said supporting means and mounted in said seat portion of said supporting means for emitting light and an optical means extending wholly along said retracting means, said supporting means or both said retracting and supporting means, for transmitting said emitted light so as to illuminate said inside of said patient's mouth, wherein said retracting means is releasably coupled to said seat portion of said support means.

2. A cheek and lip retractor according to claim 1, wherein said optical means extends from said light source along a path which when in use inside the patient's mouth, diffuses the light emitted from light source inside the mouth.

3. A cheek and lip retractor according to claim 2, wherein said retracting means comprises a polymeric transparent material shaped to said optical means and said optical means includes an external surface equipped with protrusions for diffusing the light emitted from said light source inside the mouth.

4. A cheek and lip retractor according to claim 1, wherein the illuminating device comprises, electrical supply and control means said supply means being carried by said supporting means.

5. A cheek and lip retractor according to claim 4, wherein said supply and control means comprise a battery; an electric supply circuit being apt to electrically connect the light source to the battery and extending wholly along supporting means.

6. A cheek and lip retractor according to claim 5, wherein battery is a rechargeable battery.

7. A cheek and lip retractor according to claim 1, wherein said light source comprises at least one LED.

8. A cheek and lip retractor according to claim 1, wherein said supporting means comprise an elongate supporting member with two free ends, shaped so that each of them defines a respective seat for a relative said light source; said retracting means comprising two retracting elements, each of which is connected to a relative free end.

* * * * *